(12) United States Patent
Hershberger

(10) Patent No.: US 10,483,060 B2
(45) Date of Patent: Nov. 19, 2019

(54) SURGICAL TOOL WITH AMBIDEXTROUS SAFETY SWITCH

(71) Applicant: Stryker Corporation, Kalamazoo, MI (US)

(72) Inventor: David Hershberger, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 532 days.

(21) Appl. No.: 15/267,207

(22) Filed: Sep. 16, 2016

(65) Prior Publication Data

US 2017/0000496 A1 Jan. 5, 2017

Related U.S. Application Data

(63) Continuation of application No. PCT/US2015/021379, filed on Mar. 19, 2015.
(Continued)

(51) Int. Cl.
*A61B 17/14* (2006.01)
*H01H 36/02* (2006.01)
(Continued)

(52) U.S. Cl.
CPC ............. *H01H 36/02* (2013.01); *A61B 17/14* (2013.01); *A61B 17/142* (2016.11); *A61B 90/08* (2016.02);
(Continued)

(58) Field of Classification Search
CPC ...... A61B 17/14; A61B 17/142; H01H 36/02; H01H 9/06; H01H 2009/065; H01H 2009/066; H01H 2300/014
See application file for complete search history.

(56) References Cited

U.S. PATENT DOCUMENTS

| | | | | |
|---|---|---|---|---|
| 1,876,044 | A | * | 9/1932 | Davis ...................... G01F 23/38 200/840 |
| 5,383,875 | A | * | 1/1995 | Bays ........................ H01H 3/20 200/334 |

(Continued)

FOREIGN PATENT DOCUMENTS

| CN | 101854891 A | 10/2010 |
|---|---|---|
| CN | 104271052 A | 1/2015 |

(Continued)

OTHER PUBLICATIONS

English language abstract for CN 101854891 extracted from espacenet.com database on Oct. 3, 2018, 18 pages See US equivalent U.S. Pat. No. 8,083,759.

(Continued)

*Primary Examiner* — Matthew J Lawson
(74) *Attorney, Agent, or Firm* — Howard & Howard Attorneys PLLC

(57) ABSTRACT

A powered surgical tool with a switch for regulating tool operation. A pair of opposed arms extend outwardly from opposed sides of the switch. The arms move between safety and run states. When the arms are in the safety state, the arms engage a static surface to prevent movement of the switch. When in the arms are in the run state the arms are spaced from the static surface so movement is allowed. The arms are connected together so that the movement of one arm results in simultaneous movement of the other arm.

33 Claims, 10 Drawing Sheets

Related U.S. Application Data

(60) Provisional application No. 61/968,003, filed on Mar. 20, 2014.

(51) Int. Cl.
    *B25F 5/02*     (2006.01)
    *H01H 9/06*     (2006.01)
    *A61B 90/00*     (2016.01)
    *A61B 17/00*     (2006.01)

(52) U.S. Cl.
    CPC ............... *B25F 5/02* (2013.01); *H01H 9/06* (2013.01); *A61B 2017/00477* (2013.01); *A61B 2017/00734* (2013.01); *A61B 2090/0811* (2016.02); *H01H 2009/065* (2013.01); *H01H 2300/014* (2013.01)

(56) References Cited

U.S. PATENT DOCUMENTS

| | | | | |
|---|---|---|---|---|
| 5,591,170 | A * | 1/1997 | Spievack | A61B 17/151 30/122 |
| 5,792,573 | A * | 8/1998 | Pitzen | A61B 17/1628 429/97 |
| 6,007,540 | A * | 12/1999 | Ark | A61B 17/1626 606/167 |
| 6,017,354 | A | 1/2000 | Culp et al. | |
| 6,025,568 | A * | 2/2000 | Schaeffeler | H01H 9/32 218/123 |
| 7,232,970 | B1 * | 6/2007 | Chen | H01H 9/06 200/322 |
| 7,422,582 | B2 | 9/2008 | Malackowski et al. | |
| 8,083,759 | B2 | 12/2011 | Cox et al. | |
| 8,771,300 | B2 | 7/2014 | Bare et al. | |
| 2003/0098226 | A1 * | 5/2003 | Kato | H01H 1/50 200/449 |
| 2005/0059858 | A1 * | 3/2005 | Frith | H01H 36/0006 600/118 |
| 2006/0260924 | A1 * | 11/2006 | Liu | H01H 1/2025 200/520 |
| 2006/0276114 | A1 * | 12/2006 | Gallagher | B24B 23/022 451/344 |
| 2009/0032377 | A1 * | 2/2009 | Inagaki | H01H 9/06 200/43.17 |
| 2009/0209991 | A1 | 8/2009 | Hinchliffe et al. | |
| 2012/0193199 | A1 * | 8/2012 | Chen | H01H 9/041 200/302.2 |
| 2013/0245704 | A1 | 9/2013 | Koltz et al. | |
| 2014/0338947 | A1 * | 11/2014 | Boeck | B24B 23/028 173/170 |
| 2015/0182230 | A1 * | 7/2015 | Belagali | A61B 17/14 606/82 |
| 2016/0204718 | A1 * | 7/2016 | Koizumi | B25F 5/00 318/400.18 |
| 2016/0287265 | A1 * | 10/2016 | Macdonald | A61B 90/08 |

FOREIGN PATENT DOCUMENTS

| | | |
|---|---|---|
| DE | 9320029 U1 | 6/1994 |
| DE | 10 2011 089 722 A1 | 6/2013 |
| DE | 102011089722 A1 | 6/2013 |
| WO | 03057395 A1 | 7/2003 |
| WO | 2013/177423 A2 | 11/2013 |

OTHER PUBLICATIONS

English language abstract for CN 104271052 extracted from espacenet.com database on Oct. 3, 2018, 17 pages. See US equivalent US 2013/0245704.
English language abstract for DE 102011089722 extracted from espacenet.com database on Oct. 3, 2018, 16 pages.
Chinese Office Action and Translation for Application No. 20158002367468 dated Aug. 2, 2018, 9 pages.
Machine-assisted English translation for DE 93 20 029 extracted from espacenet.com database on Dec. 6, 2017, 5 pages.
"PCT ISA Search Report and Written Opinion" for PCT/US2015/021379 dated May 2015.

\* cited by examiner

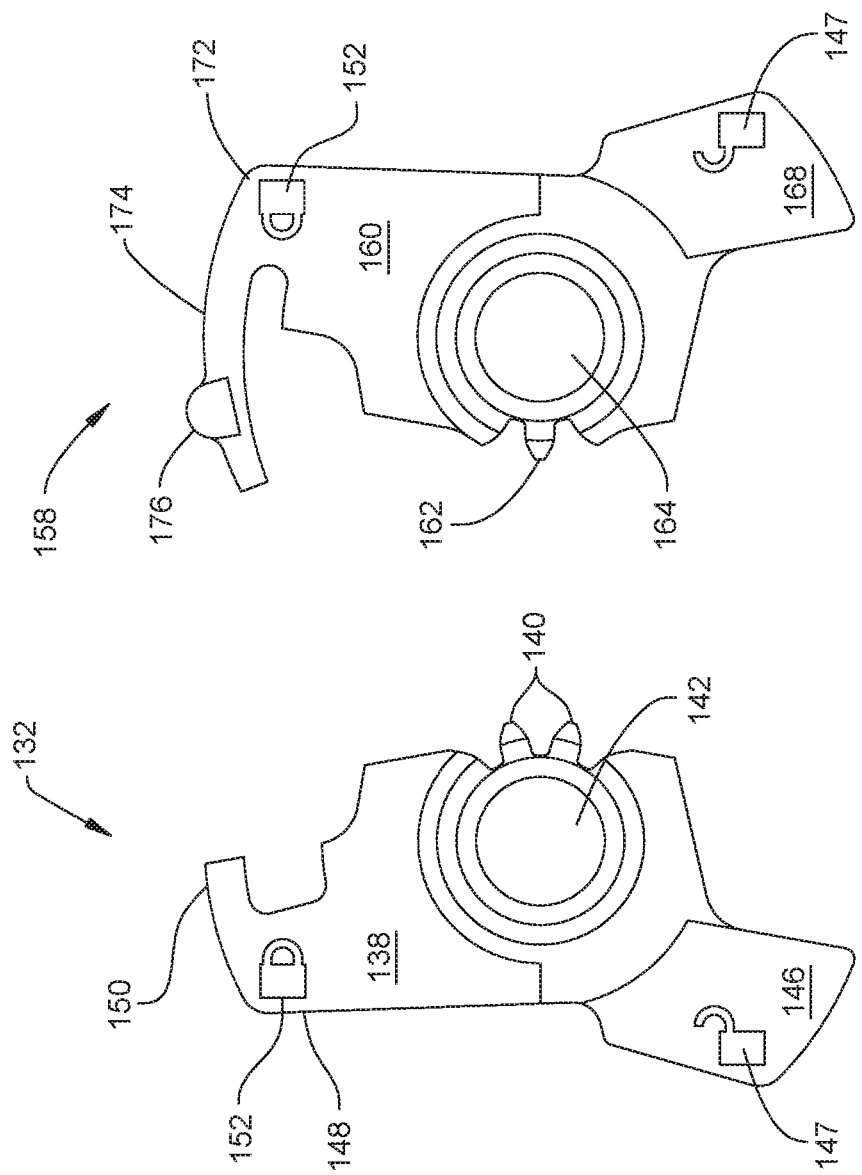

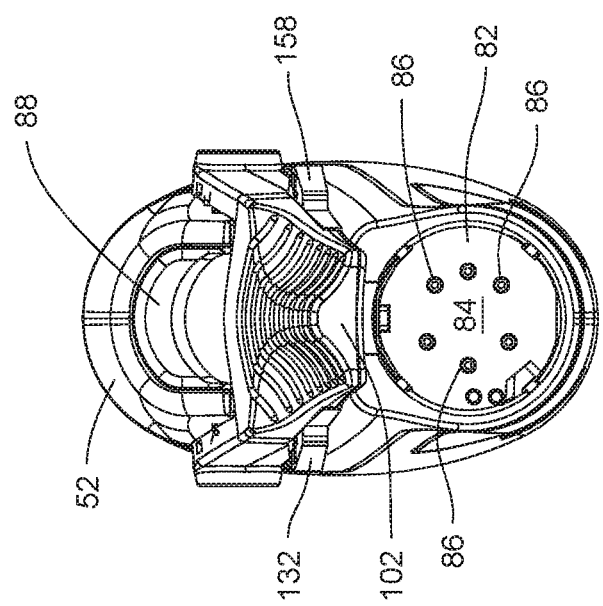

SURGICAL TOOL WITH AMBIDEXTROUS SAFETY SWITCH

FIELD OF THE INVENTION

This invention relates generally to the subject of hand held, powered surgical tools. More particularly, this invention relates to a hand held surgical tool that with a safety switch that is easily set regardless of the hand in which the tool is held.

BACKGROUND OF THE INVENTION

In modern surgery, one of the most important instruments available to medical personnel is the powered surgical tool. Often this tool is in the form of a handpiece in which a power generating unit is housed. Power generating units include, electrically driven motors, pneumatically driven motors, ultrasonic vibrators and devices that emit photonic energy (light). An energy applicator extends forward from the handpiece. If the power generating unit is a motor, the energy applicator may be a drill bit, a bur, a saw blade or a reamer. These tools are designed to be used with saw blades or blade cartridges used to separate large sections of hard and soft tissue.

The ability to use a powered surgical tool in a surgical or medical procedure lessens the physical strain of medical practitioners when performing the procedure on a patient. Moreover, most surgical procedures can be performed more quickly and more accurately with powered surgical tools than with the manual equivalents that preceded them.

Integral with the handpiece of many powered surgical tools is a hand switch or trigger. The practitioner using the tool depresses the trigger to actuate the tool power generating unit.

One such trigger switch is a lever arm switch. As implied by the name of this switch, the switch has an elongated body that, at one end, is pivotally attached to the handpiece with which the switch is associated. A spring or other biasing member holds the switch in a static position. The switch is displaced by the practitioner pressing his/her finger against a portion of the switch that is spaced from the location at which the switch is attached to the handpiece. Integral with the switch and/or handpiece is a switch sensor. The switch sensor generates a sensor signal. The sensor varies a characteristic of the sensor signal as a function of the displacement of the switch. Based on the changes in the sensor signal, a control circuit causes energization signals to be applied to the tool power generating unit that results in the actuation of the power generating unit.

The Inventor's Assignee's U.S. Pat. No. 6,017,354 issued 25 Jun. 2000 and its PCT Pat. Pub. No. WO 2013/177423 A2 published 28 Nov. 2013, both of which are explicitly incorporated herein by reference, disclose variations of a trigger switch that can be incorporated into a powered surgical tool. Mounted to the pivoting body of this switch is a magnet. Internal to the body of the handpiece to which the switch is mounted is a sensor. This sensor generates a sensor signal that varies as a function of the variations in the characteristics of the sensed magnetic field. A practitioner uses this type of handpiece by depressing the body of the trigger. This results in a movement of the magnet integral with the trigger body relative to the sensor. The sensor, in turn, outputs a sensor signal that varies as a function of the movement of the trigger magnet relative to the sensor.

A further feature of the above described trigger is that the magnet is moveably mounted to the body of the trigger. The magnet can move between a safety position and a run position. When the magnet is in the safety position, the magnet is positioned relative to the sensor that the magnetic fields emitted by the magnet are, regardless of the position of the trigger, not detectable by the sensor. Only when the magnet is in the run position is the magnet positioned close enough to the sensor actuation of the trigger results in the detectable displacement of the magnet by sensor. In an alternative version of the above assembly a bar is moveably mounted to the trigger body. The bar can be moved to and from a position in which the bar engages the handpiece. When the bar engages the handpiece, the trigger is blocked from displacement.

A benefit of the above design is that when the trigger magnet is in the safety position, the inadvertent depression of the trigger does not result in a like unintended actuation of the tool power generating unit. There is though a possibility that when the practitioner wants to use the tool, the practitioner may inadvertently not remember to move the magnet from the safety position to the run position. If this event occurs, the actuation of the trigger does not result in a like actuation of the tool power generating unit. When this event occurs, the practitioner is required to mentally process the fact that the tool did not respond to the depression of trigger switch. This practitioner is then required to conduct an investigation of the tool to understand that the reason the tool did not respond to the depression of the trigger is that the trigger is in the safety state. Once the cause of the apparent problem is understood, the practitioner moves the magnet from the safety position to the run position. Having to perform these plural distinct mental steps and then the physical step of moving the switch magnet can interrupt the practitioner's thoughts and actions regarding the steps needed to perform the procedure.

In an alternative version of the above assembly a bar is moveably mounted to the trigger body. The bar can be moved to and from a position in which the bar engages the handpiece. When the bar engages the handpiece, the trigger is blocked from displacement. This version of the trigger thus immediately provides the practitioner notice when depressing the trigger, that the trigger is in a safety state.

A limitation of the above assembly is that it has proven difficult to design the assembly so the practitioner, regardless of the hand being used to hold the handpiece can with that hand, both move the trigger in and out of the safety state and depress the trigger.

SUMMARY OF THE INVENTION

This invention is related to a new and useful powered medical or surgical tool. The power tool of this invention includes a handpiece from which an energy applicator extends. A power generating unit drives the energy applicator. Also integral with the tool of this invention is a trigger assembly for regulating the actuation of the power generating unit. The trigger of this invention has a safety feature that prevents the unintended actuation of the trigger. The tool of this invention is further designed so that, regardless of the hand in which the handpiece is held, the person using the tool can easily move the tool in and out of the safety state.

The medical or surgical tool of this invention includes a body or a shell that forms the physical handpiece held by the practitioner using the tool handpiece. The trigger assembly includes a trigger switch that is moveably mounted to the body. Two rocker arms are moveably mounted to the trigger switch. The rocker arms are located on opposed sides of the trigger switch. Each rocker arm has a tab or other member that is manually accessible and displaceable by the side of the trigger switch to which the arm is mounted. The rocker arms are interlocked such that the movement of one arm results in similar movement of the other arm. The rocker arms are moveable between a safety state and a run state. When the rocker arms are in the safety state, a structural member attached to at least one of the rock arms abuts an adjacent surface of the handpiece body. In some versions of the invention this structural member is integrally formed with the rocker arm. The abutment of this structural member against the handpiece body prevents the displacement of the trigger switch. When the rocker arms are in the run state, the structural member attached to the at least one rocker arm that abutted the handpiece body is spaced from the handpiece body.

Also part of this invention is a sensor. The sensor generates a varying signal as a function of the relative position of the trigger switch to the sensor.

When the trigger of this invention is in the safety state, the abutment of the structural component integral with at least one rocker arm against the handpiece body prevents the displacement of the trigger switch. Since the trigger switch does not move, the sensor does not undergo a state change indicating that such movement has occurred. The unintended actuation of the tool is prevented. Still another effect of the trigger switch not moving is that the practitioner, given the resistance of the switch to movement, immediately becomes aware of the fact that the trigger remains in the safety state. Minimal thought and effort is then required to reset the rocker arms to place the switch in the run state.

It is a further feature of the surgical tool of this invention that the rocker arms can be transitioned between the safety and run modes by pressing on the arm located on either side of the trigger switch. This means that the practitioner regardless of in which hand he/she is holding the handpiece can with the thumb or finger of that hand transition the tool between the safety and run states with minimal physical effort.

In many versions of the invention, the power generating unit is located in the handpiece.

In some alternative versions of the invention, the movement of the interlocking rocker arms only results in the movement of a marker attached to one of the rocker arms. A sensor integral with the handpiece monitors the position of the rocker arm.

In some versions of the invention, the rocker arms are provided with interlocking teeth. The movement of either one of rocker arms and teeth integral with that rocker arm result in the like movement of second of the rocker arms.

BRIEF DESCRIPTION OF THE DRAWINGS

The invention is pointed out with particularity in the claims. The above and further structural features and benefits of this invention are understood from the following Detailed Description taken in conjunction with the accompanying drawings in which:

FIGS. 7 and 8 are, respectively, plan and perspective views of the left side rocker arm;

FIGS. 9 and 10 are, respectively, plan and perspective views of the right side rocker arm;

FIG. 13 is a front plan view of a battery and control module with the trigger switch of this invention when the trigger is fully depressed.

DETAILED DESCRIPTION

Figure 1:
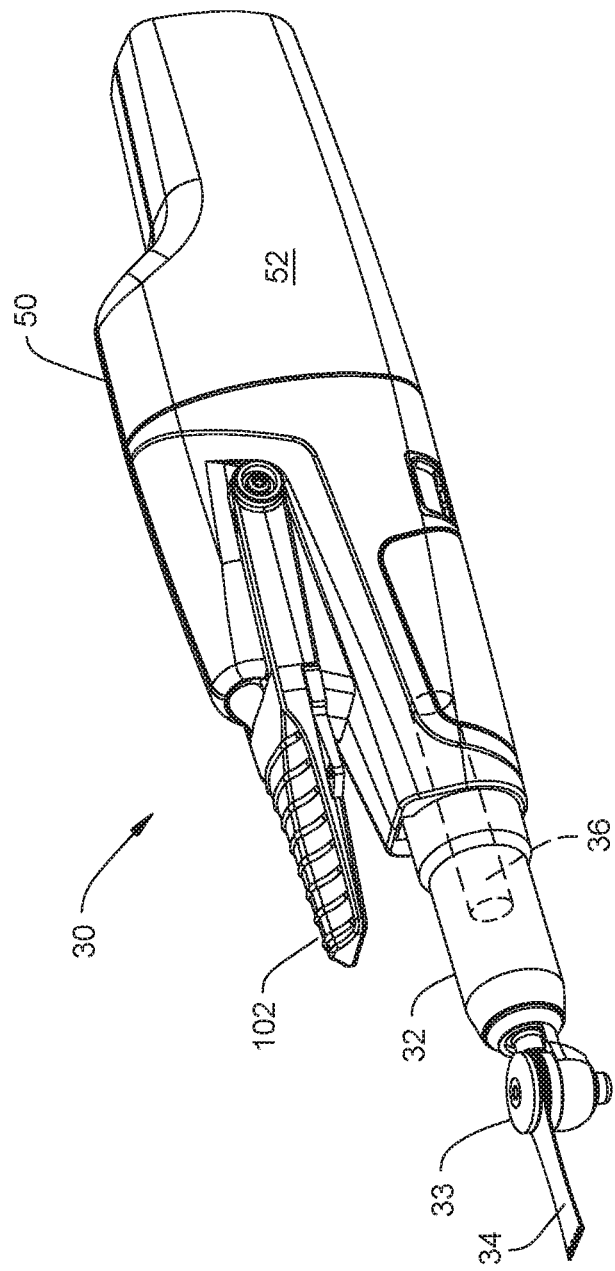
FIG. 1 is a perspective view of a powered surgical tool of this invention.

FIG. 1 depicts a powered surgical tool 30 constructed in accordance with this invention. Tool 30 is a battery powered motorized surgical tool. This particular tool 30 includes a tool unit 32 that is removably attached to a battery and control module (BCM) 50. The illustrated tool unit 32 includes a motor 36 shown as a phantom cylinder as a power generating unit. The particular tool unit is designed to oscillate a sagittal saw blade 34. In that blade 34 applies the mechanical energy output by tool motor 36 to the tissue to which the blade is applied, blade 34 is the energy applicator associated with the tool. A coupling assembly, the cap 33 of which is identified in FIG. 1, releasably holds blade 34 to tool unit 32.

Figure 2:
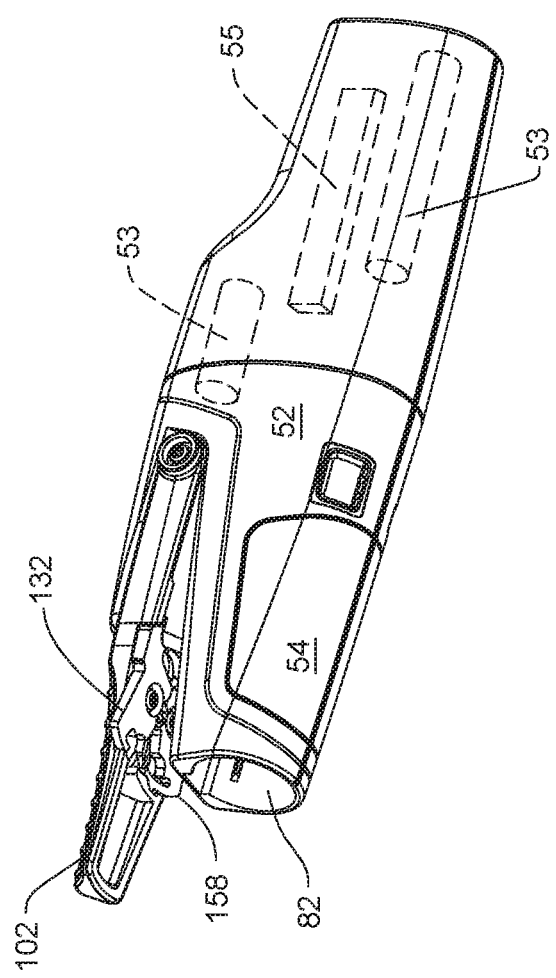
FIG. 2 is a perspective view of a battery and control module of the tool of this invention in which structural components of the switch are visible.

Internal to BCM 50 are two rechargeable cells 53 shown as phantom cylinders in FIG. 2. (In FIG. 2 and the subsequent FIGS. 3-13 the tool unit 32 is not shown so as to focus the Figures on the features of this invention.) Cells 53 provide the power for energizing the tool unit motor 36. Also internal to the BCM 50 is a tool unit controller 55, shown as a phantom rectangle. Tool unit controller 55 regulates the application of energization signals from cells 53 to the tool unit motor 36. A trigger switch 102 is moveably mounted to the BCM 50. Internal to the BCM is a sensor 198 shown as a dashed circle in FIG. 11. Sensor 198 monitors the manual actuation of switch 102. The sensor signal generated by the sensor 198 in response to the actuation of trigger switch 102 is applied to the tool unit controller 55 (connection not shown). Tool unit controller 55, in response to the actuation of the switch 102, regulates the application of energization signals from cells 53 to tool unit motor 36.

Figure 3:
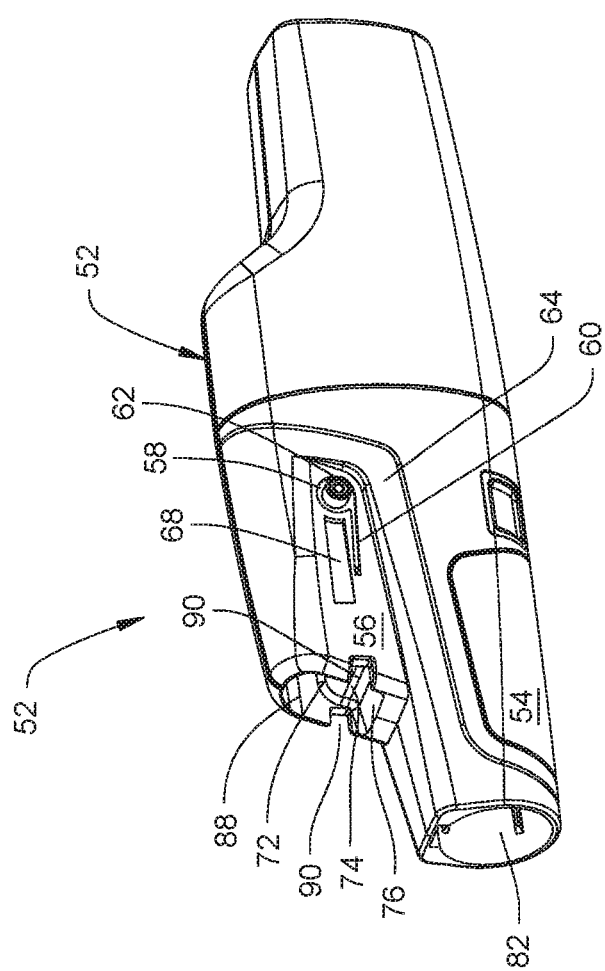
FIG. 3 is a perspective view of the outer body of the battery and control module in which the trigger switch has been removed.

From FIG. 3 it can be seen that BCM 50 has a shell 52. The shell 52 is the outer body of the tool. Shell 52 is formed from material that can both withstand the rigors of autoclave sterilization and protect the components inside the shell from the effects of autoclave sterilization. Autoclave sterilization is understood to mean exposure to an atmosphere saturated with steam (water vapor) at temperatures in excess of 125° C. at pressures of 2 bar. Shell 52 is formed so that to have at the distal end an approximately cylindrical nacelle 54. ("Distal" is understood to mean away from the surgeon holding the tool 30; towards the site to which the saw blade 34 is applied. "Proximal" means towards the surgeon holding the tool 30; away from the site to which the tool is applied.)

Two side panels 56, one seen in FIG. 3, extend upwardly from nacelle 54 at a location proximal to the distal end of the nacelle. The side panels 56 first taper inwardly and then curve into each other so as to form the top of shell 52. Each side panel 56 is formed to define a recessed surface 58. From FIG. 3 it can be seen that each recessed surface has a circular section (not identified) and an elongated section 60 that extends tangentially and distally forward from the bottom of the circular section. A boss 62 extends outwardly from the center of circular section of each recessed surface 58. A closed end bore 64 extends inwardly from the outer surface of the boss 62.

Each side panel 56 is further shaped so that there is an elongated generally rectangularly shaped notch 68 in the panel. Notches 68 extend longitudinally along the distal shell 162. Each notch 68 starts at a location a slight distance forward of the adjacent recessed surface 58. Notches 68 are present for manufacturing reasons and are otherwise not relevant to this invention.

A multi-section web extends between the opposed inner surfaces of the spaced apart side panels 56. This web is located proximal to the distal leading edges of the side panels 56. The web includes a top panel 72 that extends downwardly from the curved upper portion of the shell from which the side panels 56 extend. The web includes a step 74 that extends distally forward from the bottom of the upper panel 72. A bottom panel 76 extends forward from the distal end of step 74.

The BCM shell 52 is further shaped so that a bore 82 extends inwardly from the distal front end of the nacelle 54. Bore 82 extends through the nacelle 54 to a location proximal to web top panel 72. Bore 82 is dimensioned to receive the proximal end of the body of the tool unit 32. A web 84, seen in FIG. 13, disposed within the shell defines the closed proximal end of bore 82. Conductive pins 86 project distally forward from web 84 into bore 82. When the tool unit 32 is seated in bore 82, pins 86 seat in sockets integral with the tool unit 32 (sockets not illustrated). These pin-in-socket connections provide the necessary electrical connections between the tool unit 32 and the BCM 50. The structures of these components are not part of the present invention.

BCM shell 52 is further defined to have a cavity 88 that is located proximal to and above the distal end opening into bore 82. Specifically, cavity 88 is defined by the web consisting of upper panel 72, step 74 and bottom panel 76 and the inner surfaces of the side panels 56 located forward of these web defining surfaces. The side panels 56 are further formed so as to each have a notch 90. Each notch 90 extends rearwardly from the leading edge of the side panel 56 in which the notch is formed. Notches 90 are further located to extend into the section of shell cavity 88 immediately above bottom panel 76.

Not illustrated and not part of the present invention are the complementary features integral with the tool unit 32 and the BCM 50 that facilitate the releasable locking of the tool unit in nacelle bore 82.

Figure 4:
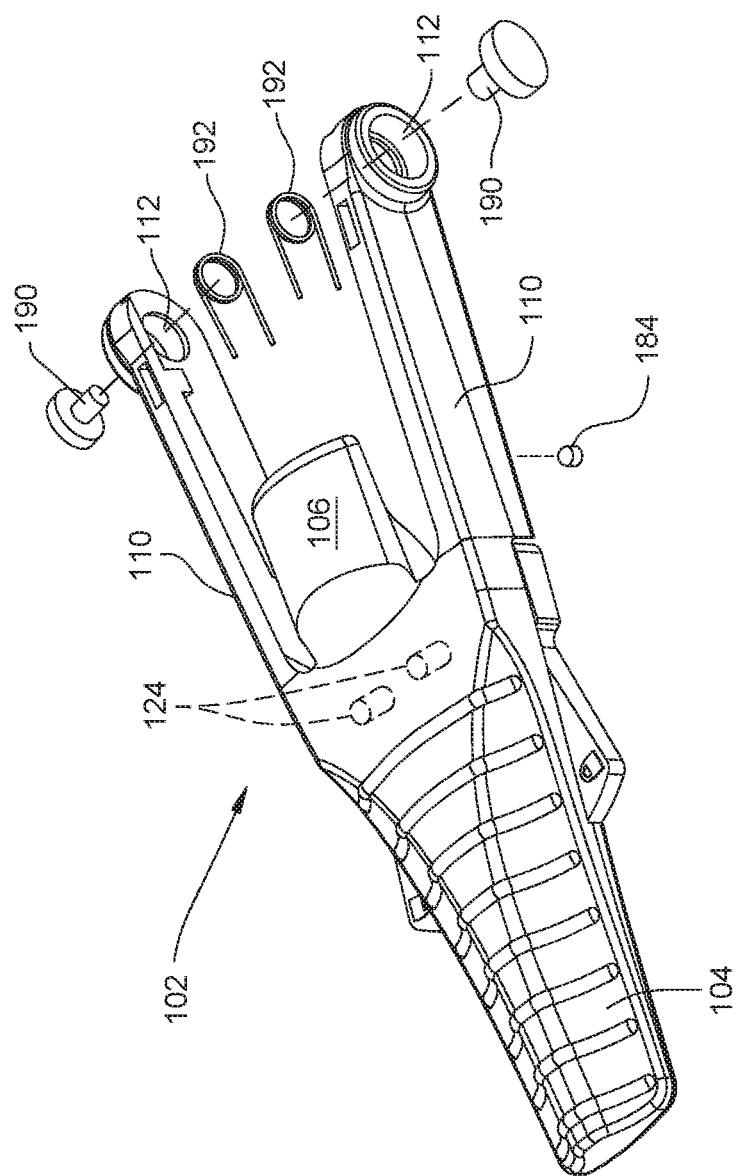
FIG. 4 is a partially exploded view of the top of the trigger switch and the components attached to the trigger switch.
Figure 5:
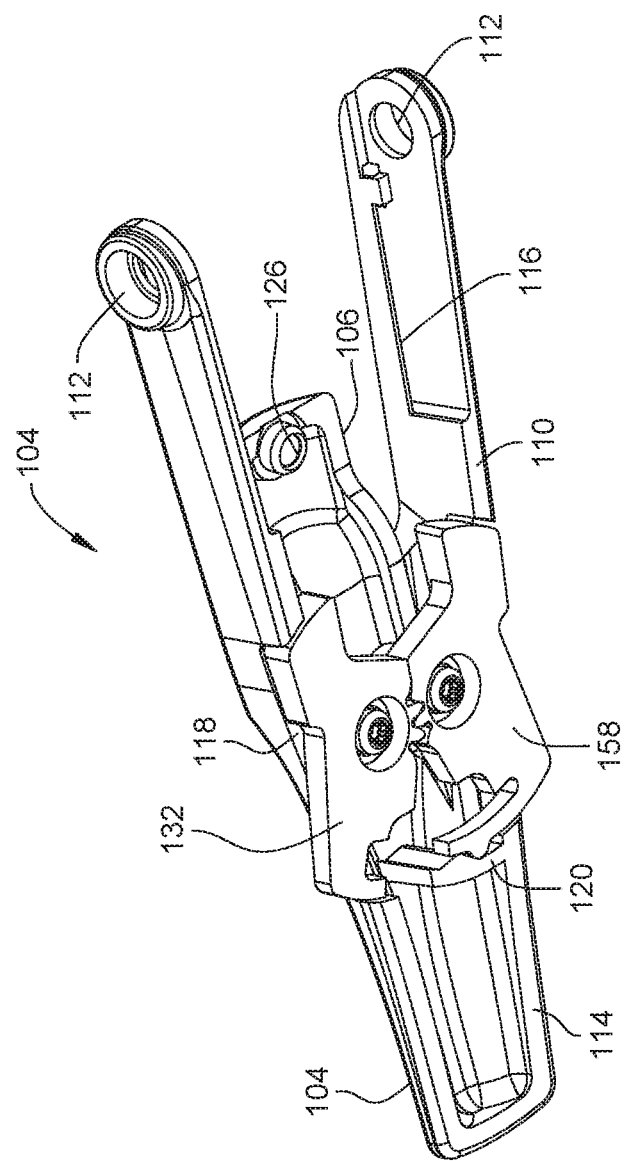
FIG. 5 is a perspective view of the underside of the trigger switch.

Trigger switch 102, as seen in FIGS. 4 and 5, is formed from a single piece of plastic able to withstand the rigors of autoclave sterilization. The switch 102 is formed to have a base 104 that is generally in the form of a truncated triangle. The base is shaped so that distal end is narrow in width. Here "width" is the dimension along a lines perpendicular to the proximal-to-distal longitudinal axis along the switch 102. Extending proximally from the distal end, the width across the base 104 gradually increases. A thumb 106 extends proximally from the proximal end of the base 104. The trigger switch 102 is formed so that the thumb 106 is elevated relative to the base 104. The trigger switch 102 is further formed so that thumb 106 can seat in and move up and down in the portion of BCM shell cavity 88 located above upper panel 72.

Two tines 110 also extend proximally away from the base 104. As each tine 110 extends proximally away from the base 104, the tine extends outwardly away from the longitudinal axis of the trigger switch. The components forming this invention are further formed so that each tine can seat against an adjacent one of the side panels 56 of the BCM shell 52. A bore 112 extends laterally through each tine 110 at a location distally forward of the proximal end of the tine. Bores 112 are coaxial.

Figure 6:
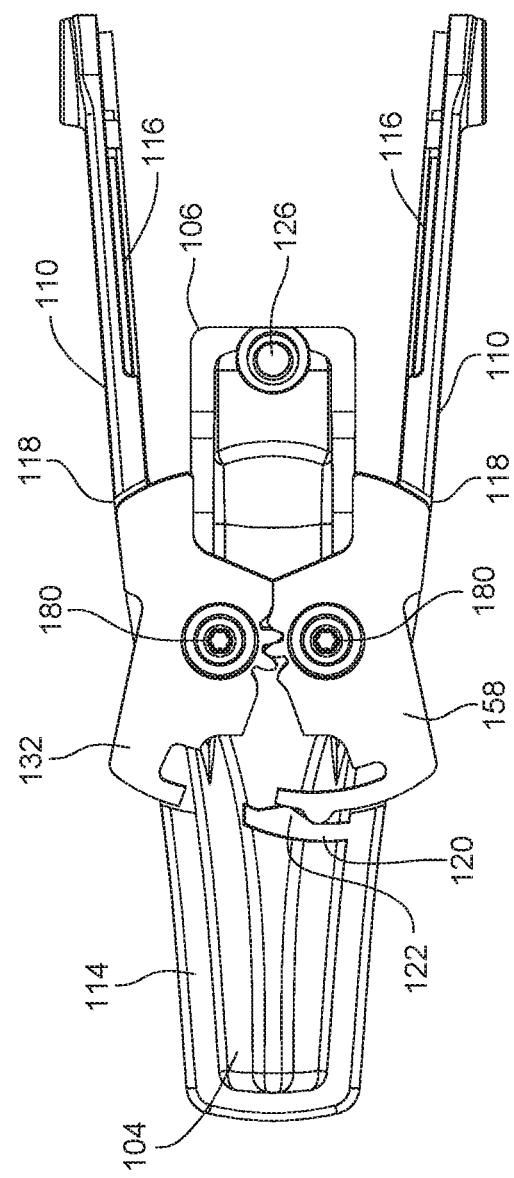
FIG. 6 is a plan view of the underside of the trigger switch.
Figure 10:
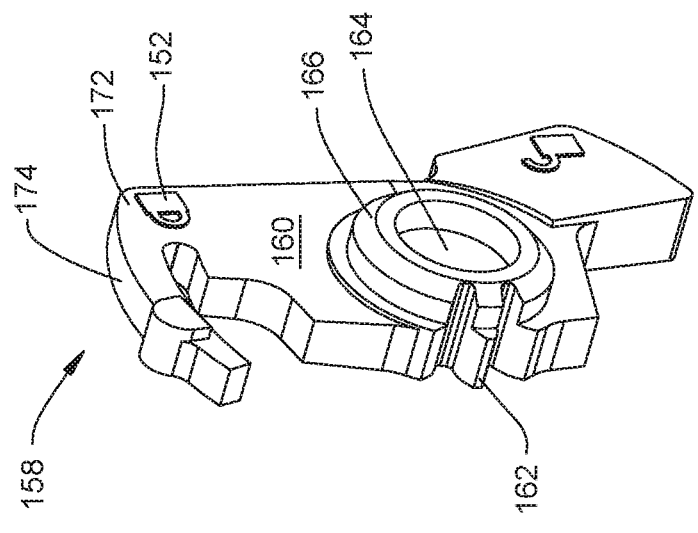
Figure 8:
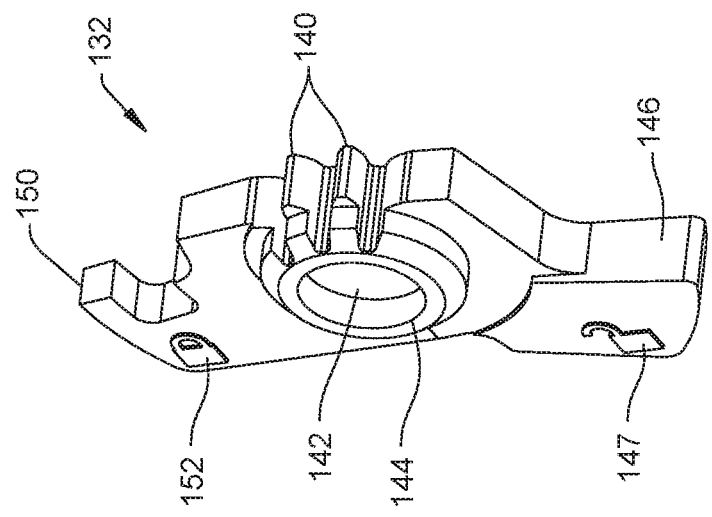

The trigger switch 102 is further formed so that a rim 114 forms the bottommost surface of the switch. The rim 114 extends from the proximal end of one tine 110 and curves into the distal end of the base 104. From the distal end of the base the rim curves proximally rearward extends along the base and terminates at the proximal end of the second tine 110. The trigger switch is further formed so that two opposed steps 116 (one identified) are formed in the rim 114. The steps 116 are formed in the sections of the rim that extend forward from the proximal ends of the tines 110. Rim 114 also has two cutouts 118 (one identified) that are diametrically opposed to each other around the longitudinal axis of the trigger switch 102. Each cutout 118 extends proximally from a portion of the rim proximal to where a tine emerges from extends from the base 104. The distal end of each cutout 118 is located in a portion of switch below the base 104. A beam 120 projects inwardly from the rim 114 on the right side of the trigger switch. In FIGS. 5 and 6 the beam 120 appears to project inwardly from the left side of the switch because the switch is inverted. Beam 120 is curved such that, as the beam extends away from the rim towards the opposed side of the trigger switch base 104, the beam curves proximally rearwardly. Beam 122 is formed to have a ridge 122 that protrudes proximally from the rest of the beam. The ridge 122 is located inwardly of the free end of the beam 120.

Trigger switch 102 is further formed to have three closed end bores that extend upwardly from the underside of the switch. Two bores 124, seen in phantom in FIG. 4, extend upwardly from the underside of the base 104. Bosses 124 are located on opposed sides of the longitudinal axis through the trigger switch 102. A third bore, bore 126, is located at the proximal end of thumb 106. Each bore 124 and 126 may be defined by a cylindrical boss formed integral with the switch 102. In the Figures only the boss that defines bore 126 is seen.

Left and right rocker arms 132 and 158 are pivotally mounted to the undersurface of the base 104 of trigger switch 102. Both rocker arms 132 and 158 are generally plate like in shape. The left rock arm 132 includes an approximately rectangular shaped center section 138. Two gear teeth 140 project inwardly from the inner edge of the center section 138, the edge of center section 138 directed to the opposed right rocker arm 158. A bore 142 extends through the center section. Bore 142 is surrounded by a rim 144 that extends circumferentially around the bore. The left rocker arm 132 is further formed so that teeth 140 extend radially outwardly from the center of bore 142

A planar tab 146 extends laterally outwardly from proximal end of arm center section 138. An icon 147 indicating that the switch is unlocked is visible on the outer surface of the thumb 146. A finger extends forward from the outer side of rocker arm center section 138. The finger consists of a proximal digit 148 and a distal digit 150. Proximal digit 148 is the portion of the finger that extends forward from the rocker arm center section 138. The distal digit 150 extends forward from the free end of the proximal digit 148. The distal digit 150 extends inwardly, toward the right rocker arm 158. The left rocker arm 132 is, however, formed so that digit 150 has a free end located inwardly of the inner edge of arm center section 138. A locked icon 152 is visible on the outer surface of the proximal digit 148

The right rocker arm 158 includes a center section 160 that is similar in shape to center section 138 of the left rocker arm 132. A difference between the two rocker arms 132 and 158 is that a single tooth 162 extends outwardly from the inner edge of the center section 160 of rocker arm 158. A bore 164 extends through center section 160. Bore 164 is surrounded by a rim 166 that projects upwardly from the center section and extends around the bore. The right rocker arm 158 is formed so that tooth 162 extends radially outwardly from the center of bore 166.

A tab 168 essentially the mirror of tab 146 extends proximally and outwardly from center section 160. Icon 147 is visible on tab 168. A finger extends forward from the outer edge of center section 160. This finger has proximal section 172 that is essentially a mirror version of the proximal digit 148 integral with the left rocker arm 132. Icon 152 is present on digit 172. A distal digit 174 of the proximal digit 172. Distal digit 174 is longer in length that the distal digit 150 integral with the left rocker arm 132. More specifically, the distal digit 174 extends outwardly beyond the inner edge of the associated arm center section 160. Distal digit 174 has a curved profile. The right rocker arm 158 is further formed so that a rib 176 extends forward from the distally directed face of the distal digit 174.

When the trigger assembly of this invention is assembled, each rocker arm 132 and 158 is positioned so that the arm bore 142 or 164 is in registration with the appropriate bore 124 of the trigger switch base 104. Each rim 144 and 166 seats around the boss that defines the associated bore 124. Fasteners 180, identified in FIG. 6, that extend through arm bores 142 and 164 into the underlying bores formed in the boss 124 pivotally hold the rocker arms 132 to switch 102. When the trigger switch is so assembled, right rocker arm tooth 162 meshes with left rocker arm teeth 140.

A magnet 184, seen in FIG. 4, is seated in bore internal to the boss 126 that extends downwardly from the underside of thumb 106.

Fasteners 190, also seen in FIG. 4, pivotally secure the trigger switch 102 to BCM shell 52. Each fastener 190 extends through one of the bores formed in one of the switch tines and into an adjacent one of the bores 64 formed in the shell 52. A torsion spring 192 is disposed around each fastener. One arm of each torsion spring 192 is seated in the elongated recessed section 60 formed the adjacent shell side panel 56. The opposed arm of the torsion spring 192 seats against the step 116 of the adjacent tine 110. Torsion springs 192 bias the trigger switch 102 so the distal end of the switch is normally pivoted away from the underlying nacelle 54 of the BCM shell 52. Finger force is sufficient to overcome the force that holds the trigger switch way from the nacelle 54.

The trigger assembly of this invention also includes a sensor 198. Sensor 198, represented by a dashed circle in FIGS. 11 and 12, monitors the displacement of trigger switch 102. Since the depicted trigger switch is pivotally mounted to the BCM shell 54, sensor 198 monitors this movement. In the described version of the invention the sensor monitors variations in a nearby magnetic field. More particularly, the sensor 198 is disposed in the shell to monitor the variations in the magnetic field emitted by magnet 184 mounted to trigger switch 102. In this version of the invention, the sensor 198 is mounted in the portion of the shell below step 74. In versions of the invention in which the sensor 198 outputs a signal that changes as a result of the displacement of magnet 184, the sensor 198 may be a Hall effect sensor or a magneto resistive resistor.

Sensor 198 outputs a signal representative of the displacement of the trigger switch 102. The signal produced by sensor 198 is applied to tool controller 55. Based at least partially on the sensor signal, the tool controller 55 regulates the application of energization signals from cells 53 to tool unit motor 36. The means by which tool controller 55 regulates the application of energization signals to the motor 36 is not part of the present invention.

A tool 30 of this version of the invention is prepared for use by inserting the tool unit 32 in the battery and control module 50. As a result of this connection, tool controller 55 is able to selectively apply energization signals to the tool unit motor 36 so as to actuate the motor.

Normally, torsion springs 192 hold the trigger switch 104 in a position so that magnet 184 is spaced away from sensor 198. Sensor 198, in turn, outputs a sensor signal representative of the magnet field emitted by magnet 184 when the trigger switch is in this state. Tool controller 55 interprets this sensor signal as indicating that the switch is not displaced, and that use of the tool is not required. When the tool controller 55 determines that the trigger switch is in this state the tool controller does not actuate source energization signals to the tool unit that result in the actuation of motor 36.

There may be times when the practitioner wants to prevent unintended actuation of tool 30. At these times, the practitioner sets the rocker arms 132 and 158 to the safety state. The practitioner performs this activity by pressing inwardly on one of the rocker arm tabs 146 or 168. This results in the rotation, the pivoting, of the rocker arm 132 or 158 integral with the depressed tab 146 or 168, respectively. Owing to the engagement of left rocker arm teeth 140 with right rocker arm tooth 162, the rotation of either one of the rocker arms 132 or 158 results in a like rotation of the other rocker arm 158 or 132. Rocker arms 132 and 158 are thus simultaneously rotated so that tabs 146 and 168 retract inwardly from the side edges of the triggers switch base 104. The retraction of tabs 146 and 168 result in icons 147 being concealed under switch base 104.

Figure 11:
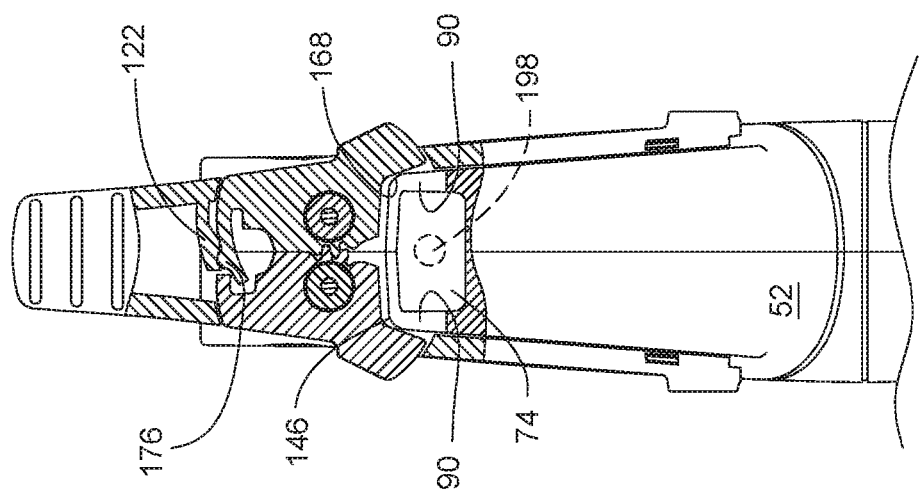
FIG. 11 is a partial cross sectional view of the trigger assembly of this invention when the assembly is in the safety state.

This rotation of the tabs 146 and 168 results in each tab seating in a separate one of the notches 90 formed in the BCM shell 52 as seen in FIG. 11. The seating of tabs 146 and 168 in notches prevents the pivotal movement of the trigger switch 102. More particularly, if there is attempt to pivot the switch, tabs 148 abut the rigid surfaces of module body 52 that define notches 90. At this time, the trigger switch is in the safety state. This means that the unintended application of force to trigger switch 102 does not result in the pivoting of the switch and resultant displacement of the magnet 184. Since the magnet 184 is locked from unintended movement, sensor 198 does not output a sensor signal that incorrectly indicates that the trigger switch has been intentionally depressed and that the motor 36 should therefore be actuated.

A further feature of the rocker arms moving to the safety state is that the rib 176 integral with the distal digit 174 of the right rocker arm is rotates to the right past ridge 122 integral with trigger switch beam 120. To undergo this transit, the rocker arm distal digit 174 flexes. The resultant abutment of the digit rib 176 against the trigger switch ridge 122 means that, unless force is applied to rotate the rocker arms, the arms will not move out of the safety state.

Also as result of the rocker arms 132 and 158 rotating to the safety state, proximal digits 148 and 172 rotate outwardly away from the side edges on the base 104 of the switch. Lock icons 152 are thus visible.

Figure 12:
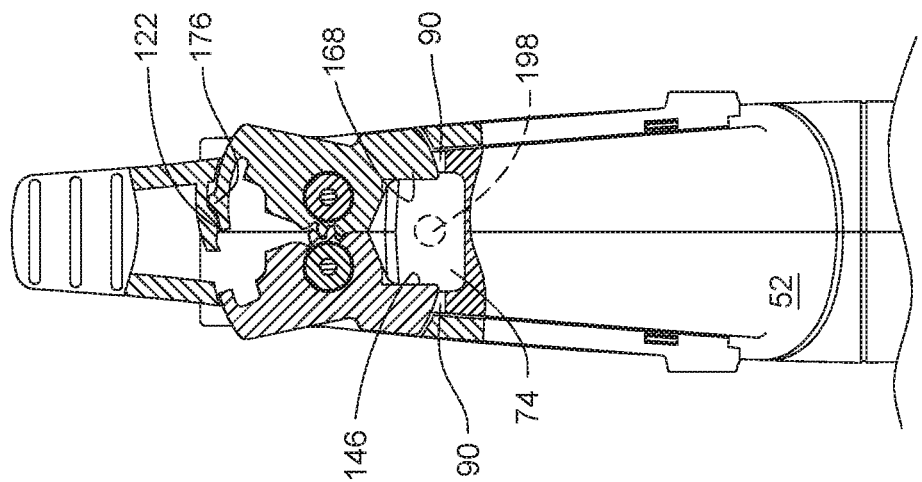
FIG. 12 is a partial cross sectional view of the trigger assembly of this invention when the assembly is in the run state.

When it is time to use tool unit 30, the practitioner first moves the trigger from the safety state to the run state. The practitioner performs this task by applying finger or thumb force to either one of the proximal digits 148 or 172. Again, owing to the engagement of teeth 140 with tooth 142, regardless of which digit 148 or 172 is depressed, the rocker arms simultaneously rotate. This force applied by the practitioner is sufficient to flex right rocker arm distal digit 174 so rib 176 can move beyond switch ridge 122. As a result of the rotation of the rocker arms, tabs 146 and 168 rotate clear of notches 90 as seen in FIG. 12. The movement of the tabs 146 and 168 out of notches 78 places the trigger switch 102 in the run state.

As a result of the pivoting of rocker arm fingers into the space below the trigger switch base, the locked icons 152 become concealed. The simultaneous pivoting of tabs 146 and 168 outwardly from the sides of the base 104 of the trigger results in the exposure of the unlocked icons 147.

Once trigger switch 102 is in the run state, the downward force of practitioner's thumb or finger on the trigger switch overcomes the force of the torsion springs 192. Trigger switch 102, including magnet 184, pivots downwardly as seen in FIG. 13. This results in a change in the characteristics of the magnet field adjacent sensor 198. Sensor 198 in turn, outputs a sensor signal representative of the characteristic of the change in the magnetic field, the change in position of the trigger switch. The tool controller 55, at least partially based on the change in the sensor signal, then applies energization signals from the cells to the tool motor as is appropriate.

The tool 30 of this invention is designed so that, regardless of which rock arm 132 and 158 the practitioner pivots to transition the switch between the safety and run states, the other rocker arm 158 and 132 undergoes a like movement. This means that regardless with which hand a tool of this invention is held, the practitioner, with the thumb or fingers of that hand, can easily move the switch between the safety and run states.

Another feature of this invention is that when the trigger switch 102 is in the safety state, the switch is physically blocked from being displaced. Should a practitioner attempt to actuate the tool when the switch is in the safety state the switch will not move. The resistance to which the practitioner is exposed provides the practitioner immediate tactile feedback that the switch is in the safety state. Mentally the practitioner is immediate aware of the fact that, if use to the tool is desired, the switch needs to be transitioned out of the safety state in into the run state. No time is lost having to study the switch to determine that the reason the tool did not run when the handpiece was actuated was due to the failure to take the switch out of the safety state.

The trigger assembly of this invention is further designed so that when the rocker arms are moved between the safety and run states, some resistance must be overcome to move the rib 176 integral with the right rocker arm 158 past the ridge 122 internal to the switch base 104. Exposing the practitioner to this momentary increase in resistance provides tactile feedback that the switch has undergone the transition to the desired switch state.

The above is directed to one specific surgical tool of this invention. The invention may have constructions different from the described version.

For example, the tool of this invention is not limited to tools that include tool units that are removably attached to complementary battery and control modules. Thus, the switch of this invention may be built into a tool the body or shell of which includes both the tool power generating unit and the control circuit that regulates the actuation of the tool.

Similarly, the tool of this invention is not limited to battery powered surgical tools. Alternative tools of this invention may include control console from which the energization signals are sourced to the tool power generating unit. These tool and control console assemblies are disclosed in the incorporated by reference U.S. Pat. No. 6,017,354 as well as the now incorporated by reference U.S. Pat. No. 7,422,582 issued 9 Sep. 2008. Still other tools of this invention may not include a power generating unit that is located internal to the tool. The power generating unit is located in the remote console to which the tool is attached. The signal from the sensor representative of switch state is forwarded to the console. Based on the state of this signal, the console selectively actuates the power generating unit.

Likewise, in some versions of the invention, components of the trigger of this invention may be built into assemblies that are separate from each other. Thus, the trigger switch and attached rocker arms could be built into a base unit that is removably attached to a shell or body. This shell or body services as the housing in which the other components of the tool including the power generating unit, the control circuit and the switch sensor are mounted. Thus, as discussed in the incorporated by reference U.S. Pat. No. 6,017,354 the switch may be mounted to a unit that is removably attached to the tool. A tool of this version of the invention can be used by practitioners that do not prefer a tool with the control switch mounted to the tool body. These practitioners rely on foot pedal to control the tool operation. If a practitioner prefers a tool mounted control switch, the switch assembly is removably attached to the tool Further, there is no requirement that in all versions of the invention, the trigger switch be designed to pivot relative to the static component, the base unit, of the tool to which the switch is attached. In some versions of the invention the switch may slide. In these and other versions of the invention, the components integral with the rocker arms that seat in a complementary notch formed in the base unit may not be substantially planar with the portions of the rocker arms that are depressed to pivot the arms. Thus in these versions of the invention, the structural members that perform the function of tabs 148 and 168 can be in planes that are angled relative to the portions of the arms from which these structural members extends.

As discussed above, the movement of either one of the rocker arms results in a like movement of the other rocker arm. This means that in some versions of the invention it may be necessary to provide only a single one of the rocker arms with a structural component that engages a complementary feature of the base unit to prevent movement of the switch. Likewise, in some versions of the invention, one or both arms may drive a link or other member. This driven link or other member is the component that selectively engages or is spaced away from surface of the tool to selectively inhibit or allow switch movement.

Components other than gear teeth may be incorporated into this invention to ensure that the displacement of one of the rocker arms results in a like movement of the other rocker arm For example, the simultaneously movement of the rocker arms may be the result of providing a friction fit between the rocker arms. Alternatively, a belt or chain that extends between the arms may transfer the motion applied to one of the arms to the other arm.

It is within the scope of this invention to provide assemblies other than ridge 122 and rib 176 that inhibit unintended movement of the arms 132 and 158. For example, in some versions of the invention, the moveable component that moves when finger force is applied to arm may be attached to the switch as opposed to one the arms. In some versions of the invention, the complementary components that engage each other may be formed on the arms. In other words one arm may have a resilient component of feature that engages a component associated with the second arm. In these and other versions of the invention, both components may be resilient so as to be able to both be able to move. Likewise there is no requirement that in all versions of the invention the components be made resilient by making the components flexible. In some versions of the invention a spring or other component may provide the resiliency that returns to the component to the state in which the component inhibits unintended arm movement.

Further the switch assembly of this invention is not limited to assemblies where a magnetic field sensor is employed to monitor the displacement of the trigger switch relative to the base unit. In some versions the sensor that monitors the displacement of the trigger switch may be of different from. For example in some versions of the invention, the sensor may be some sort of potentiometer. The displacement of the trigger switch results in a change in a position of the wiper integral with the potentiometer. This would result in a change of voltage across the potentiometer. In other versions of the invention, the sensor may optically sense the displacement of the trigger switch. In still other versions of the invention, the displacement of the switch may displace a plunger. The movement of the plunger is monitored by a detecting member such as a coil. The signal from this plunger displacement detecting member thus functions as the signal representative of the displacement of the trigger switch.

Similarly, it should be understood that the power generating unit integral with the tool need not always be an electrically driven motor. Other tools of this invention may have other power generating units such as: pneumatically driven motors; hydraulically driven motors; ultrasonic vibrators; photonic energy (light emitting) components; RF generators; and electrodes that emit heat or electrical energy. Similarly it should be understood that the energy applicator need not always be separate from the power generator. Electrosurgical tools that sink/source current are in this category of surgical tool. The energy applicators of these tools are different from the described saw blade.

In some tools of this invention it may not be possible to releasably attach the energy applicator to the tool body.

In this Detailed Description, the trigger switch of this invention is described as being part of a tool used to perform medical or surgical procedures. It should be understood that the switch of this invention may be incorporated into other products that perform different tasks. These products include products designed for industrial, automotive, aeronautical, marine and military applications.

Accordingly, it should be understood that the appended claims cover all such variations and modifications that cover the true spirit and scope of this invention.

What is claimed is:

1. A powered surgical tool, the powered surgical tool including:
   a tool body;
   an energy applicator that extends forward from the tool body, the energy applicator adapted to receive energy from a power generating unit and apply the energy to tissue to which the energy applicator is applied; and
   a switch assembly attached to the tool body for controlling the actuation of the power generating unit, the switch assembly including:
   a switch that is moveably mounted to the tool body;
   a sensor configured to generate a signal representative of the position of the switch relative to the sensor;
   two arms that are pivotally mounted to said switch such that said arms extend outwardly from opposed sides of the switch and each arm is capable of moving from a safety state to a run state; and
   a member attached to at least one of said arms such that when said arm is in the safety state, the member engages a fixed surface to prevent movement of said switch and, when said arm is in the run state, the member is spaced from the fixed surface so that said member does not impede movement of the switch and
   wherein, said switch assembly is further constructed so that each said arm includes a base that is pivotally mounted to said switch and the bases of said arms are formed with components that engage each other, so that the pivoting of either one of the arm bases from the arm run state to the arm safety state, results in the simultaneous pivoting of the other arm base from the arm run state to the arm safety state, and the pivoting of either arm base from the arm safety state to the arm run state results in the simultaneous pivoting of the other arm base from the arm safety state to the arm run state.

2. The powered surgical tool of claim 1, wherein said member that engages a fixed surface to prevent movement of said switch is a section of at least one of said arms.

3. The powered surgical tool of claim 2 wherein each said arm has a said section that engages a fixed surface to prevent movement of said switch.

4. The powered surgical tool of claim 1, wherein said arms are mounted to said switch so that each said arm has:
   a first section that extends from said base that, when said arms are in the run state, is concealed by said switch and, when said arms are in the safety state, is exposed; and
   a second section that extends from said base that, when said arms are in the run state, is exposed and, when said arms in the safety state, is concealed by said switch.

5. The powered surgical tool of claim 1, wherein said arm components that engage each other to the cause the simultaneous pivoting of said arms are interlocking teeth.

6. The powered surgical tool of claim 1, wherein said arm components that engage each other to cause the simultaneous pivoting of said arms consists of: a friction fit between the arms; a belt that extend between the arms; or a chain that extends between the arms.

7. The powered surgical tool of claim 1, wherein said switch is attached to said tool body so as to be able to pivot.

8. The powered surgical tool of claim 1, wherein said switch or a said arm is formed with a component that engages the other arm or said switch to resist movement of the associated said arm, said component being resiliently attached to said switch or said arm so that the resistance imposed by said component can be overcome by force applied to the said arm.

9. The powered surgical tool of claim 8, wherein said component that engages the other arm or said switch is attached to one of said arms.

10. The powered surgical tool Of claim 9, wherein said switch is formed with a feature that engages said arm component to resist pivoting of the said arm to which said component is attached.

11. The powered surgical tool of claim 1, wherein:
said switch assembly is further formed to include a structural member to which said switch is moveably attached and said structural member is formed to define a notch; and
said member of at least one said arm that engages a fixed surface is positioned to when the said arm to which said member is attached is in the safety state, seat in the notch formed in said structural member of said switch assembly to prevent movement of said switch and, when the said arm to which said member is attached is in the run state, be spaced away from the notch.

12. The powered surgical tool of claim 1, wherein said switch assembly is configured to be removably attached to said tool body.

13. The powered surgical tool of claim 1, wherein the power generating unit is contained in said tool body.

14. The powered surgical tool of claim 13, wherein the power generating unit is: an electrically driven motor; a pneumatically driven motor; a hydraulically driven motor; an ultrasonic vibrator; a device that emits light; an RF generator; a device that emits heat; or a device that emits electrical energy.

15. The powered surgical tool of claim 1, wherein:
the power generating unit is contained in said tool body;
a module is attached to said tool body, said module containing a controller that controls the application of energization signals to the power generating unit; and
said switch assembly is attached to the module.

16. The powered surgical tool of claim 1, wherein:
a magnet is mounted to said switch; and
said sensor monitors the strength of the magnetic field emitted by said magnet.

17. The powered surgical tool of claim 1, wherein said tool body includes a coupling assembly that releasably holds the energy applicator to the tool body.

18. A powered surgical tool, the powered surgical tool including:
a tool body;
an energy applicator that extends forward from the tool body, the energy applicator adapted to receive energy from a power generating unit and apply the energy to tissue to which the energy applicator is applied; and
a switch assembly attached to the tool body for controlling the actuation of the power generating unit, the switch assembly including:
a switch that is moveably mounted to the tool body;
a sensor configured to generate a signal representative of the position of the switch relative to the sensor;
two arms that are pivotally mounted to said switch such that said arms extend outwardly from opposed sides of the switch and each arm is capable of moving from a safety state to a run state wherein said arms are connected together so that the pivoting of either said arm from the run state to the safety state results in the simultaneous pivoting of the other said arm from the run state to the safety state and the pivoting of either said arm from the safety state to the run state results in the simultaneous pivoting of the other said arm from the safety state to the run state; and
each said arm has a first tab that, when said arms are in the run state, is concealed by said switch and, when said arms are in the safety state, is exposed; and
a second section that, when said arms are in the run state, is exposed and, when said arms in the safety state, is concealed by said switch; and
a member attached to at least one of said arms such that when said arm is in the safety state, the member engages a fixed surface to prevent movement of said switch and, when said arm is in the run state, the member is spaced from the fixed surface so that said member does not impede movement of the switch.

19. The powered surgical tool of claim 18, wherein said member that engages a fixed surface to prevent movement of said switch is a section of at least one of said arms.

20. The powered surgical tool of claim 19, wherein each said arm has a said section that engages a fixed surface to prevent movement of said switch.

21. The powered surgical tool of claim 18, wherein said arms include complementary engaging teeth that cause the simultaneous pivoting of said arms are interlocking teeth.

22. The powered surgical tool of claim 18, wherein said arms are connected together to cause the simultaneous pivoting of said arms by one of: a friction fit between the arms; a belt that extend between the arms; or a chain that extends between the arms.

23. The powered surgical tool of claim 18, wherein said switch is attached to said tool body so as to be able to pivot.

24. The powered surgical tool of claim 18, wherein said switch or a said arm is formed with a component that engages the other arm or said switch to resist movement of the associated said arm, said component being resiliently attached to said switch or said arm so that the resistance imposed by said component can be overcome by force applied to the said arm.

25. The powered surgical tool of claim 24, wherein said component that engages the other arm or said switch is attached to one of said arms.

26. The powered surgical tool Of claim 25, wherein said switch is formed with a feature that engages said arm component to resist pivoting of the said arm to which said component is attached.

27. The powered surgical tool of claim 18, wherein:
said switch assembly is further formed to include a structural member to which said switch is moveably attached and said structural member is formed to define a notch; and
said member of at least one said arm that engages a fixed surface is positioned to when the said arm to which said member is attached is in the safety state, seat in the notch formed in said structural member of said switch assembly to prevent movement of said switch and, when the said arm to which said member is attached is in the run state, be spaced away from the notch.

28. The powered surgical tool of claim 18, wherein said switch assembly is configured to be removably attached to said tool body.

29. The powered surgical tool of claim 18, wherein the power generating unit is contained in said tool body.

30. The powered surgical tool of claim 29, wherein the power generating unit is: an electrically driven motor; a pneumatically driven motor; a hydraulically driven motor; an ultrasonic vibrator; a device that emits light; an RF generator; a device that emits heat; or a device that emits electrical energy.

31. The powered surgical tool of claim 18, wherein:
the power generating unit is contained in said tool body;

a module is attached to said tool body, said module containing a controller that controls the application of energization signals to the power generating unit; and said switch assembly is attached to the module.

32. The powered surgical tool of claim 18, wherein:

a magnet is mounted to said switch; and said sensor monitors the strength of the magnetic field emitted by said magnet.

33. The powered surgical tool of claim 18, wherein said tool body includes a coupling assembly that releasably holds the energy applicator to the tool body.

* * * * *